United States Patent [19]
Littig

[11] Patent Number: 5,888,234
[45] Date of Patent: Mar. 30, 1999

[54] SHUTTLE LOCK

[75] Inventor: David H. Littig, Ventura, Calif.

[73] Assignee: United States Manufacturing Company, Pasadena, Calif.

[21] Appl. No.: 895,462

[22] Filed: Jul. 16, 1997

[51] Int. Cl.⁶ ........................................................ A61F 2/80
[52] U.S. Cl. ................................ 623/38; 623/27; 623/33; 623/34
[58] Field of Search ................................ 623/27, 33, 34, 623/35, 36, 37, 38

[56] References Cited

U.S. PATENT DOCUMENTS

| | | | |
|---|---|---|---|
| 5,047,063 | 9/1991 | Chen | 623/38 |
| 5,226,918 | 7/1993 | Silagy et al. | 623/38 X |
| 5,376,129 | 12/1994 | Faulkner et al. | 623/33 |
| 5,507,837 | 4/1996 | Laghi | 623/33 X |
| 5,728,170 | 3/1998 | Becker et al. | 623/37 |
| 5,759,206 | 6/1998 | Bassett | 623/27 |

FOREIGN PATENT DOCUMENTS

WO91/15169  10/1991  WIPO ...................................... 623/38

OTHER PUBLICATIONS

Prosthetic Design, Inc., "Refinforced Shuttle Locks," p. 40.
Century XXII Innovations, Inc., "Commonly Asked Questions," 1 page.
Otto Bock Orthopadische Industrie, "Einfach besser: der Otto Bock Silicon Liner," 2 pages.
PEL, Fillauer "3S Silicone Suction Socket," 3 pages.
PEL, ALPS, "Silicone Suction Socket," 1 page.
PEL, Iceross™, "Silicone Suction Socket," 1 page.

*Primary Examiner*—Michael J. Milano
*Assistant Examiner*—Tram A. Nguyen
*Attorney, Agent, or Firm*—Christie, Parker & Hale, LLP

[57] ABSTRACT

A shuttle lock for a below-knee prosthesis comprising a body portion having a vertically extending hole for receipt of a pin from a roll-on suction suspension sleeve located within a socket, and a cup-shaped flange positioned on a upper surface of the body portion for receipt of the socket to provide on-axis alignment of the pin to the shuttle lock. The shuttle lock further includes a sprag clutch for engagement and disengagement of the pin.

9 Claims, 3 Drawing Sheets

SHUTTLE LOCK

FIELD OF THE INVENTION

This invention relates generally to prosthetic devices, and more particularly, to a shuttle lock positionable on a distal socket having a cup-shaped flange to provide on-axis alignment of a pin from a suspension sleeve to the body of the shuttle lock.

BACKGROUND OF THE INVENTION

Various types of foot and leg prosthetic devices are well known in the art. Such devices frequently include some form of attachment for coupling the device to the distal end of the limb of the amputee and for extending to the ground to provide body support. Leg prosthesis are generally of two types, being an above knee prosthesis and a below knee prosthesis. One form of below-knee prosthesis is fabricated as an assembly having a flexible roll-on suction suspension sleeve, a socket, a shuttle lock, a lower leg component and a foot. The shuttle lock provides rigid attachment of the suspension sleeve to the socket and lower leg component.

Some currently available shuttle lock components utilized in below-knee prosthesis designs consist of a ratchet style or clutch style cylindrical body portion having a hole for receipt of the suspension sleeve pin. The body includes a release button to disengage a gear located within the body from the pin.

A problem with existing types of shuttle lock designs is that the cylindrical body must become intregal and permanently molded to the prosthetic socket during fabrication. If the cylindrical body is improperly positioned during fabrication, the pin may not align easily and consistently with the shuttle lock latching mechanism. The only alternative is either to refabricate the socket, which can be time consuming and generate additional costs, or try to train the patient to overcome the difficulty he faces in donning the prosthesis.

Consequently, there exists a need for a new and improved shuttle lock for a below knee prosthesis that can be positioned and repositioned at any time on the distal socket to provide on-axis alignment of the pin to the body of the shuttle lock to alleviate patient frustration and eliminate rejection of an improperly aligned socket.

SUMMARY OF THE INVENTION

The present invention provides a shuttle lock for a below-knee prosthesis which eliminates the problems of prior existing shuttle lock devices, and is easy and inexpensive to manufacture.

Briefly, the shuttle lock of the present invention includes a body section having a vertically oriented hole for receipt of a pin from a suspension sleeve and a horizontally extending hole for the receipt of a sprag clutch. The sprag clutch extends into the vertically extending hole for engagement and disengagement of the pin. The body includes an enlarged base portion having a four hole pattern for attachment to a modular pylon system or other lower leg prosthetic componetry. Positioned on the top portion of the body is a cup-shaped flange for receipt of the lower surface of a prosthetic socket which allows the socket to be positionable during the alignment process by the prosthetist. The flange includes a plurality of set screws to securely lock together the socket with the shuttle lock once alignment is established. The shuttle lock, comprising the body section, the base and the cup-shaped flange can be manufactured as an integral component, or can be manufactured as separate components connected by suitable hardware.

These and other aspects of the invention will be more fully described in the following detailed description and the accompanying drawings.

DETAILED DESCRIPTION

Figure 1:
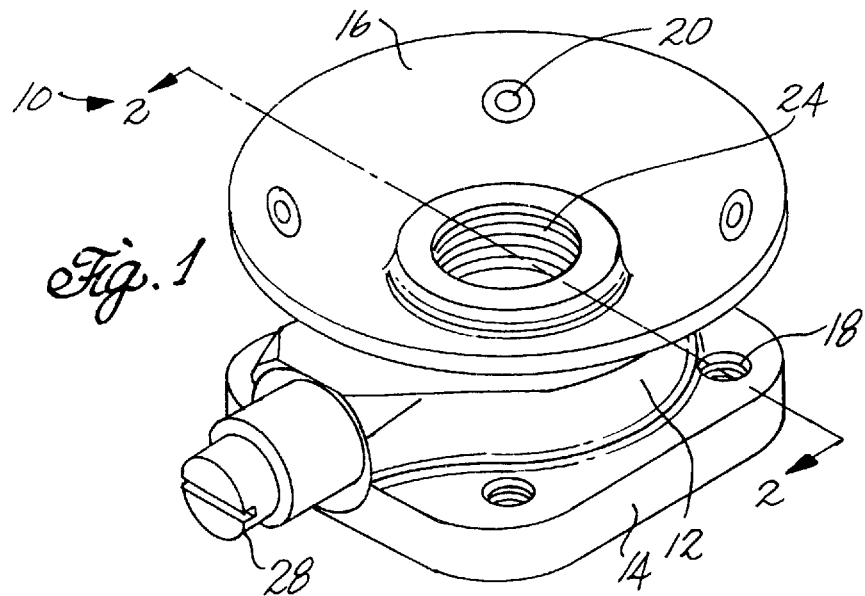
FIG. 1 is a perspective view showing one embodiment of the shuttle lock of the present invention.
Figure 2:
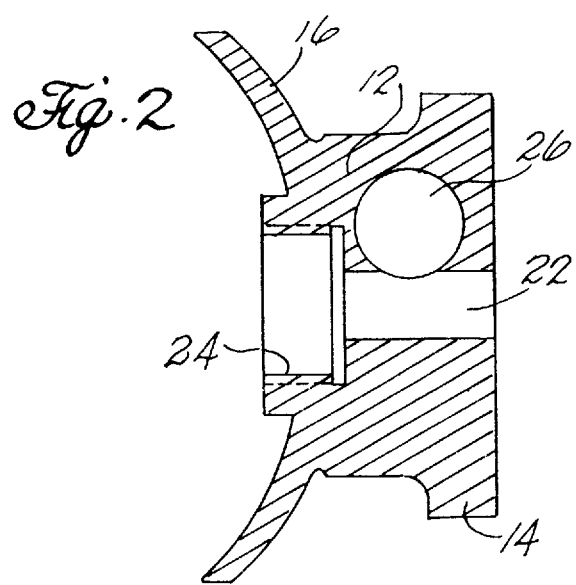
FIG. 2 is a cross-sectional view taken along line 2—2 of the shuttle lock of FIG. 1.

FIG. 1 is a perspective view of the shuttle lock 10 of the present invention. The shuttle lock is preferably made from a high-strength aluminum alloy. As also shown in FIG. 2, the shuttle lock 10 includes a generally cylindrical body portion 12 having a square base 14 and a cup-shaped upper flange 16 located on the upper portion of the shuttle lock. The base 14 includes a universal 4-hole pattern 18 for distal lower leg component attachment. The cup-shaped flange includes four equally spaced set screws 20 to securely lock together the shuttle lock with a prosthetic socket (FIG. 3) to be discussed in more detail below.

Figure 3:
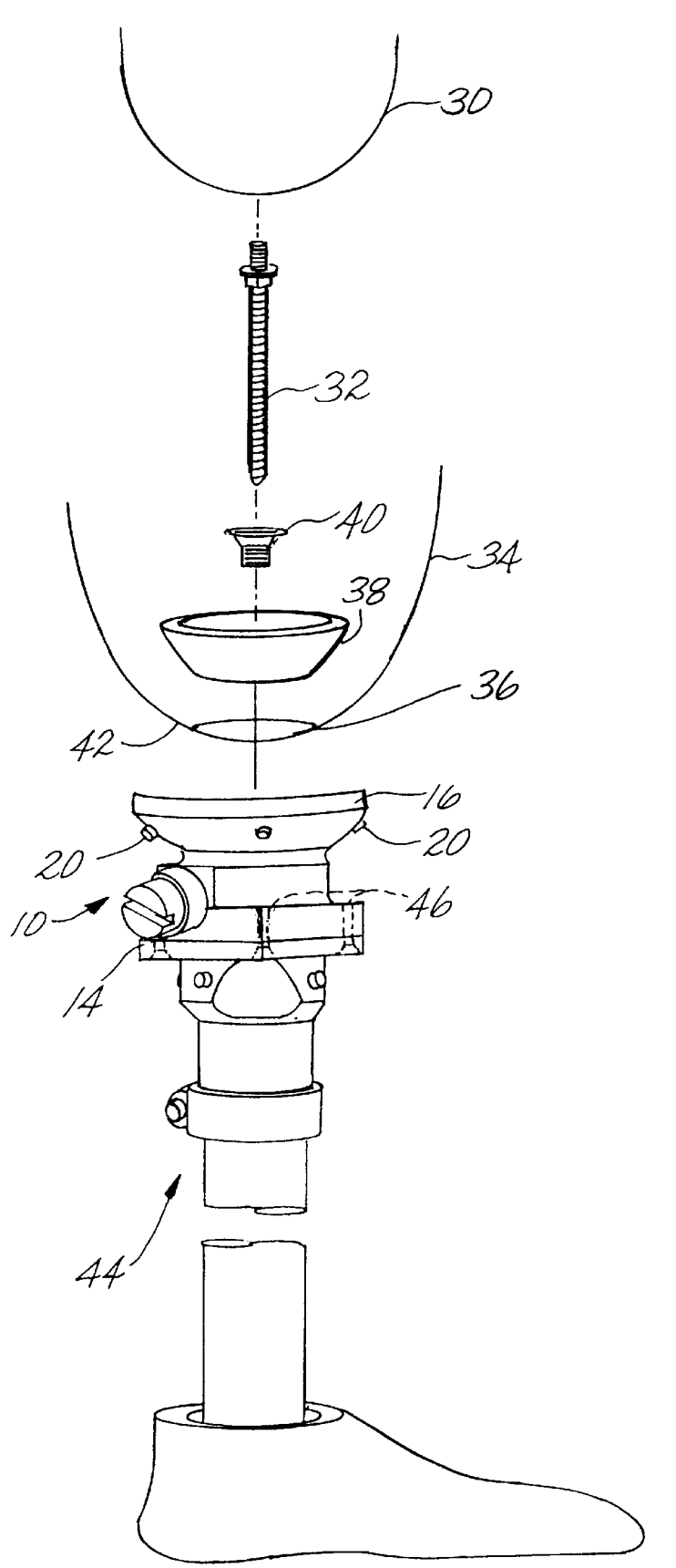
FIG. 3 is an exploded front view of the shuttle lock of FIG. 1 as incorporated into a below knee prosthesis.

The shuttle lock includes a centrally located vertically extending hole 22 for receipt of a pin on a suction suspension sleeve (FIG. 3). The upper portion 24 of vertical hole 22 is threaded and enlarged for receipt of a screw (FIG. 3) for further attachment of the prosthetic socket. The body portion 12 includes a horizontally extending hole 26 for receipt of a sprag clutch 28 to engage and disengage the pin of the suspension sleeve.

Referring now to FIG. 3, the shuttle lock 10 of the present invention is shown as incorporated into a typical below knee prosthesis 28. A roll-on suction suspension sleeve 30, typically made of silicone, is rolled onto the limb (not shown) of the amputee. The suspension sleeve has a metal pin 32 integrally connected to the sleeve for receipt within the vertical hole of the shuttle lock. The suspension sleeve is placed within a plastic socket 34 having an enlarged opening 36 in its lower surface for passage of the pin 32. A dish 38 also including an opening for passage of the pin, is located in the bottom of the socket to guide the pin 32 through the opening 36 of the socket and into vertical hole 22 of the shuttle lock. A cylindrical screw 40 having a dish shaped head is positioned within the opening in dish 38 and threads into the top portion 24 of the shuttle lock to further rigidly connect the socket to the shuttle lock once alignment has been established during the fitting process.

The shuttle lock 10 is positioned below the socket 34 such that the bottom surface 42 of the socket seats within flange 16, and pin 32 extends through vertical hole 22 and engages a sprag clutch 28. The base 14 of shuttle lock is rigidly secure to lower leg componetry such as a modular pylon system 44 by screws 46 extending through the universal 4-hole pattern.

The advantages of the present invention is that the shuttle lock does not involve permanent integration into the socket. The shuttle lock is an after-fabrication component that can be used with the socket. The curved cup-shaped flange engages the lower surface 42 of the socket to provide angulation between the two components for proper alignment by the prosthetist. Once the alignment is established, screw 40 is tightened followed by tightening set screws 20 to securely lock the socket to the shuttle lock. Set screws (which are pointed to dig into the plastic socket) prevent unwanted rotation. The alignment concept allows for positioning and repositioning of the socket to provide on-axis alignment of the pin to the shuttle lock. The shuttle lock can be used in combination with a test socket to determine the exact alignment configuration which can then be transferred to a permanent socket manufactured in either a laminate or thermoplastic having the precise contours of the users limb.

Figure 4:
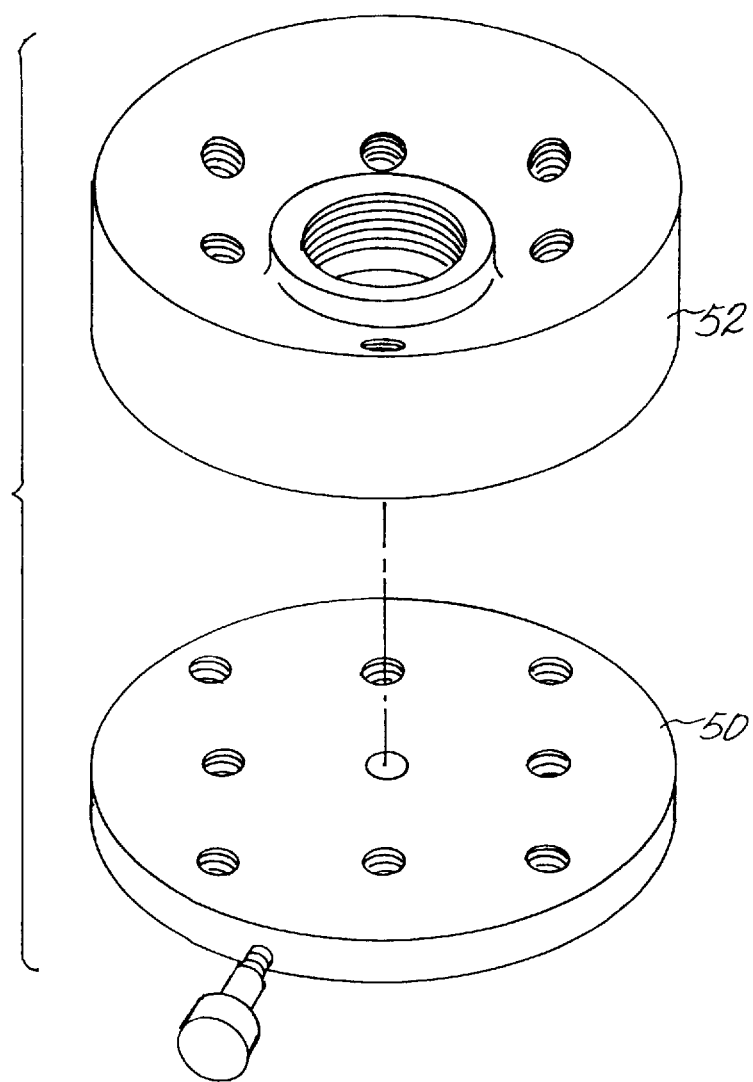
FIG. 4 is a perspective view of an alternative embodiment of the present invention.

The preferred embodiment shuttle lock of the present invention is manufactured as a one-piece integral component comprising the body, base and cup-shaped flange, however the shuttle lock can be manufactured as separate components as shown in FIG. 4. In FIG. 4, the body portion 50 and the cup-shaped flange 52 are separate components which would be rigidly secured together by suitable hardware such as bolts. In this embodiment, the cup-shaped flange could be combined with shuttle locks of other manufacturers.

Although the present invention has been described and is illustrated with respect to two embodiments thereof, it is to be understood that it is not to be so limited since changes and modification may be made therein which are within the full intended scope of this invention as hereinafter claimed.

What is claimed:

1. A shuttle lock for a below-knee socket comprising:

a body portion; and means for providing on-axis alignment of the below-knee socket with the body portion, wherein the means for providing on-axis alignment is adjustable relative to, and non-integral with, the socket, wherein the below knee socket includes a roll-on suction sleeve having a pin extending through the socket, wherein the on-axis alignment means is a cup-shaped flange positioned above the body portion of the shuttle lock for receipt of the socket to align the pin to the body portion, and wherein the body portion has a vertically extending hole for receipt of the pin.

2. The shuttle lock of claim 1 wherein the body portion further includes a horizontal channel intersecting the vertical hole for receipt of a clutch for engaging the pin.

3. The shuttle lock of claim 1 wherein the flange and the body portion are integral.

4. The shuttle lock of claim 1 wherein the flange includes a plurality of set screws for fastening the shuttle lock to the socket.

5. A below-knee prosthesis comprising:

a roll-on suction suspension sleeve having a pin extending from a lower portion thereof;

a socket having an opening on a lower surface for receipt of the pin;

a shuttle lock located below the socket having a vertically extending opening for receipt of the pin;

means for providing on-axis alignment of the pin to the shuttle lock; and a lower leg component positioned below the shuttle lock, wherein the means for providing on-axis alignment is adjustable relative to, and non-integral with, the socket, and wherein the on-axis alignment means is a cup-shaped flange extending upwardly from the shuttle lock for receipt of the socket to align the pin to the shuttle lock.

6. The below-knee prosthesis of claim 5 wherein the flange and the shuttle lock are integral.

7. The below-knee prosthesis of claim 5 wherein the flange includes a plurality of set screws for fastening the shuttle lock to the socket to prevent rotation of the socket.

8. The below-knee prosthesis of claim 5 wherein the shuttle lock further includes a horizontal channel intersecting the vertical opening for receipt of a clutch mechanism for engaging the pin.

9. The below-knee prosthesis of claim 5 further including a dish positioned in the socket below the suction sleeve for guiding the pin toward the shuttle lock.

* * * * *